United States Patent [19]
Blau et al.

[11] 4,430,319
[45] Feb. 7, 1984

[54] RADIOACTIVE IODINE LABELED PHENOLIC AMINES

[75] Inventors: Monte Blau, Buffalo; Hank F. Kung, Amherst; Kenneth M. Tramposch, East Amherst, all of N.Y.

[73] Assignee: State University of New York, Albany, N.Y.

[21] Appl. No.: 380,720

[22] Filed: May 21, 1982

[51] Int. Cl.³ .................... A61K 43/00; A61K 49/00
[52] U.S. Cl. .......................................... 424/1.1; 424/9; 422/61; 564/105; 564/280; 564/305
[58] Field of Search ............... 424/1, 1.5, 9; 564/105, 564/280, 305; 422/61

[56] References Cited

U.S. PATENT DOCUMENTS

| | | | |
|---|---|---|---|
| 4,088,747 | 5/1978 | Hunt et al. | 424/1 |
| 4,091,088 | 5/1978 | Hunt et al. | 424/1 |
| 4,120,867 | 10/1978 | Akerkar et al. | 260/326.4 |
| 4,202,874 | 5/1980 | Akerkar et al. | 424/1 |
| 4,254,056 | 3/1981 | Konno et al. | 564/387 |
| 4,279,887 | 7/1981 | Baldwin et al. | 424/1 |
| 4,284,619 | 8/1981 | Un | 424/1 |
| 4,308,249 | 12/1981 | Frank et al. | 424/1.5 |
| 4,310,675 | 1/1982 | Akerkar et al. | 548/336 |
| 4,314,081 | 2/1982 | Molloy et al. | 564/347 |
| 4,347,382 | 8/1982 | Scharver | 424/1 |
| 4,352,751 | 10/1982 | Wieder et al. | 424/1 |
| 4,360,511 | 11/1982 | Baldwin et al. | 424/1.5 |

OTHER PUBLICATIONS

Tramposch et al., J. Nucl. Med., Jun. 1981, p. P12.
Winchell et al., J. Nucl. Med., 21:940-946 (1980).
Winchell et al., J. Nucl. Med., 21:947-952 (1980).

*Primary Examiner*—Christine M. Nucker
*Attorney, Agent, or Firm*—Michael L. Dunn; Howard M. Ellis

[57] ABSTRACT

The invention is accomplished by the formation at the site of use of the radioactive amine of the invention which is then injected immediately into the mammal for diagnostic purposes. The compounds of the invention are as follows:

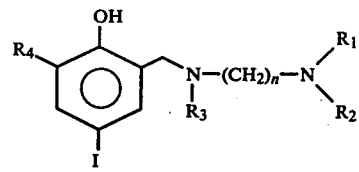

In the above compound, $R_1$, $R_2$, $R_3$ and $R_4$ are independently any straight or branched alkyl of between 1 and about 10 carbons; n may be between 1 and about 20.

In the invention, the radio labeling of the invention compound is accomplished immediately prior to use of the radio labeled material. The compounds of the invention when boiled for about 15 minutes with iodine-123, a radioactive material, undergo a substitution of radioactive for non-radioactive iodine such that the compound becomes labeled and suitable for use. The compound itself, prior to radio labeling, is storage stable.

27 Claims, 1 Drawing Figure

RADIOACTIVE IODINE LABELED PHENOLIC AMINES

The invention described herein was made in the course of work under a grant or award from the Veteran's Administration.

FIELD OF THE INVENTION

The present invention is directed to a method for selectively depositing, for diagnostic purposes, radiopharmaceutical compounds in target tissues or organs of a mammal. Mammal as used herein includes the human being. The invention more particularly relates to radiopharmaceutical compounds which are capable of selective accumulation in tissues or organs having lowered intracellular pH as a result of normal metabolism or diseased state.

PRIOR ART

Radiopharmaceutical compounds have been in use for diagnostic purposes for a long time. Those well versed in the art relating to radiopharmaceuticals and nuclear medicine are well aware of the requirements which must be satisfied by a diagnostically useful radiopharmaceutical compound. Briefly, these requirements include the following. The radiopharmaceutical compound must be able to penetrate into a target tissue or organ and attain a sufficiently high concentration therein so that its presence is detectable by state of the art radiation monitoring means. The accumulation of the radiopharmaceutical compound in the target tissue or organ must be sufficiently selective relative to other tissues and organs of the body so that a diagnostic distinction for its presence in the target tissue or organ relative to the other tissues or organs can be made. Furthermore, the radiopharmaceutical compound must emit radiation capable of penetrating through several other tissues or organs of the body. Experience has shown that only radiopharmaceutical compounds emitting gamma rays, X-ray or position radiation satisfy this requirement. Finally, and preferably, a diagnostic radiopharmaceutical compound should be easily prepared from inexpensive and available radionuclides.

In order to gain the desired tissue or organ penetration and uptake specificity for a radiopharmaceutical compound, various physiological processes and phenomena have been exploited in the past. For example, radioactive compounds which are excreted or detoxified by the liver or kidney may accumulate in these organs long enough for permitting a diagnosis of liver or kidney malfunctions. Other radiopharmaceutical compounds may depend on a selective transport mechanism through the cell membranes for entry into the cells of the target tissue or organ. An example of such a compound is F-18 2-fluoro-2-deoxyglucose which, being a close structural analog of the ubiquitous metabolite glucose, enters cells through the existing active transport mechanism for glucose. Once inside the cell, F-18 2-fluoro-2-deoxyglucose undergoes phosphorylation to yield the corresponding 6-phosphate. F-18 2-fluoro-2-deoxyglucose 6-phosphate, however, does not enter the conventional metabolic pathways of glucose 6-phosphate and due to its state of ionization, is incapable of rapidly exiting from the cells by passive diffusion through the cell membranes. Consequently, it is effectively trapped within the cells. F-18 2-fluoro-2-deoxyglucose, by mimicking the natural metabolite glucose, is capable of crossing the blood brain barrier and therefore has been found suitable for radiopharmaceutical mapping of the brain. The structures of radiopharmaceutical compounds, depending upon selective transport mechanisms, are obviously very limited since the cell must recognize the structure of the compound as being desirable for the cell.

Another example of a radiopharmaceutical compound which freely crosses cell membranes and thereafter is rather effectively trapped within the cells is N-13 labeled ammonia. After entry into the cells, N-13 labeled ammonia is enzymatically converted into amino acids and other metabolites which are incapable of diffusing out of the cell. For a detailed description of the biodistribution and metabolism of F-18 2-fluoro-2-deoxy-glucose and N-13 labeled ammonia reference is made to the following publications:

Gallagher B M, Fowler J S, Gutterson N I, et al: Metabolic Trapping as a Principle of Radiopharmaceutical Design: Some Factors Responsible for the Biodistribution of ($^{18}$F) 2-deoxy-2-fluoro-D-glucose, J. Nucl. Med. 19:1154-1161, 1978; Phelps M E, Hoffman E J, Rayband C: Factors which Affect Cerebral Uptake and Retention of $^{13}$NH$_3$, Stroke 8: 694-701, 1977; Gallagher B M, Ansari A, Atkins H., et al: Radiopharmaceuticals XXVI. $^{18}$F-labeled 2-deoxy-2-fluoro-D-glucose as a Radiopharmaceutical for Measuring Regional Myocardial Glucose Metabolism in vivo: Tissue Distribution and Imaging Studies in Animals, J. Nucl. Med. 18: 990-996, 1977; Carter C C, Lifton J F, Welch M J: Oxygen Uptake and Blood pH and Concentration Effects of Ammonia in Dogs Determined with Ammonia Labeled with 10 Minutes Half-lived Nitrogen-13, Neurology 23: 204-213, 1973; Phelps M E, Hoffman E J, Selin C, et al: Investigation of ($^{18}$F) 2-fluoro-2-deoxyglucose for the Measure of Myocardial Glucose Metabolism, J. Nuc. Med. 19: 1311-1319; Tewson T J, Welch M J, Raichle M E: ($^{18}$F)-Labeled 3-deoxy-3-fluoro-D-glucose: Synthesis and Preliminary Biodistribution Data, J. Nuc. Med. 19: 1339-1345 (1978).

In the above cited article authored by Phelps et al, Stroke 8: 694-701, 1977, it was recognized that ammonia is capable of penetrating the blood brain barrier only in the form of free ammonia (NH$_3$) and not as ammonium ion. Furthermore, this article has reiterated the teachings of the prior art that a strong correlation exists between lipid solubility characteristics of a compound, as measured by oil-water partition coefficients, and the blood brain barrier penetration capability of the compound. A significant disadvantage of radiopharmaceuticals bearing F-18 labeled fluorine or N-13 labeled nitrogen is that these radionuclides are not generally available.

Other radiopharmaceutical compounds have been designed which take advantage of lipid solubility to permit the compound to enter the organ or tissue. See e.g. Michael D. Loberg et al: Membrane Transport of Tc-99m-Labeled Radiopharmaceuticals. I. Brain Uptake by Passive Transport: J. Nucl. Med. Vol. 20, No. 11, pp. 1181-1188. Most of the compounds described in the Loberg et al article nevertheless have ionic substituents and have no means for enhancing their retention within the cellular structure of the organ or tissue. Other such compounds use various isotopes of iodine as the radioactive component (radionuclide) of the radiopharmaceutical compound. Some of such iodine containing compounds are believed to have taken advantage of lipid solubility in order to enter the cell and, although not recognized in the prior art, some may have even inherently been held within an organ or tissue due to a drop in pH. An example of such a prior art iodine containing compound which may have such previously unrecognized properties is 1,4,-(di-methylamino)methyl-3-iodobenzene.

It has been proposed that the iodophenylalkyl amines be labeled with I-123 for use in brain studies, the Journal of Nuclear Medicine, Vol. 21, No. 10, p. 940 and Vol. 21, No. 10, p. 947. These materials, although successful in use, are difficult to form. Further, the iodine-123 has a half life of only about 13 hours. Therefore, these iodophenylalkyl amines are difficult to use as the radioactive iodine must be ordered by the user and then formed into these iodophenylalkyl amines by means of sophisticated laboratory techniques at a supplier and immediately shipped to the site where it is to be used. With the short half-life of the iodine, these compounds are not totally satisfactory as a waste of the expensive radioactive iodine takes place by the delays in shipping and use.

Therefore, there remains a need for a compound and method which will permit the rapid formation and use of I-123 labeled amine compounds for use as a radiopharmaceutical compound for diagnostic purposes.

BRIEF DESCRIPTION OF THE INVENTION

It is an object of this invention to overcome disadvantages of prior materials.

Another object of this invention is to provide a lower cost diagnostic radiopharmaceutical.

A further object of this invention is to provide a method of synthesis of a new compound particularly suitable for use with pharmaceutical diagnostics.

It is another object of this invention to provide a material which allows scintiphotos to be made a short time after injection of the radioactive compound but does not allow radioactive buildup in the body to a harmful extent.

It is another object of this invention to provide a new radioactive compound and an easy method of formation of such compound.

These and other objects of the invention are generally accomplished by the formation at the site of use of the radioactive amine of the invention which is then injected immediately into the mammal for diagnostic purposes. The compounds of the invention are as follows:

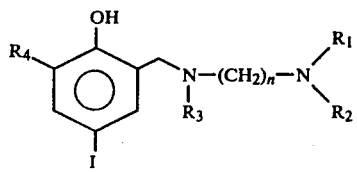

In the above compound, $R_1$, $R_2$, $R_3$ or $R_4$ are independently at each occurrence a straight or branched alkyl of between 1 and about 10 carbons; n may be between 1 and about 20.

An optimum compound for the invention is the compound as shown below:

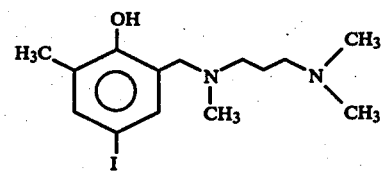

In the invention, the radio labeling of the compound is accomplished immediately prior to use of the radio labeled material. The compounds of the invention when boiled for about 15 minutes with iodine-123 (I-123), a radioactive material, undergo a substitution such that the compound becomes labeled and suitable for use. The compound itself, prior to radio labeling, is storage stable.

MODES OF PRACTICING THE INVENTION

Figure 1:
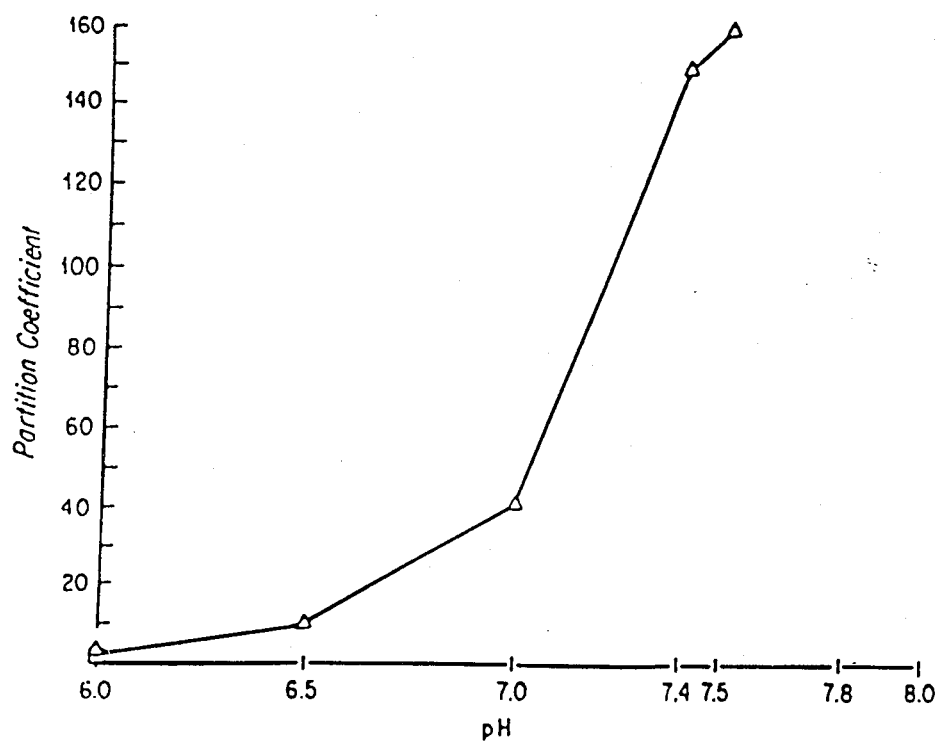
FIG. 1 is a graph showing n-octanol-aqueous medium partition coefficient pH correlation of an optimum compound of the present invention.

The system of the invention has numerous advantages over prior radiopharmaceuticals. The compounds of the invention are suitable for single photon emission computed tomography (SPECT) imaging as it emits gamma rays with a gamma energy of 159 KeV. which is suitable for SPECT systems. Because of the short half-life of the the iodine-123 and the lack of retention in the body of the invention compound, it delivers a low patient radiation dose and has a high rapid initial brain uptake and stable intracerebral distribution pattern for the required duration of the imaging procedures which is about 1 hour. Further, and of special interest in this invention, is that the invention allows the easy preparation of the radioactive agent from a kit in most nuclear medicine clinics. To achieve the isotope incorporation, one merely has to heat the salt of the amine of the invention in deionized water containing the radioiodide (iodine-123) and the substitution of the isotope takes place creating a radiopharmaceutical suitable for immediate use. These and other advantages of the invention will become apparent from the description as given below.

The synthesis of the compounds of the invention is illustrated in general by the diagrammatic structure below:

Synthesis of Ring Alkyl Iodophenol Diamines

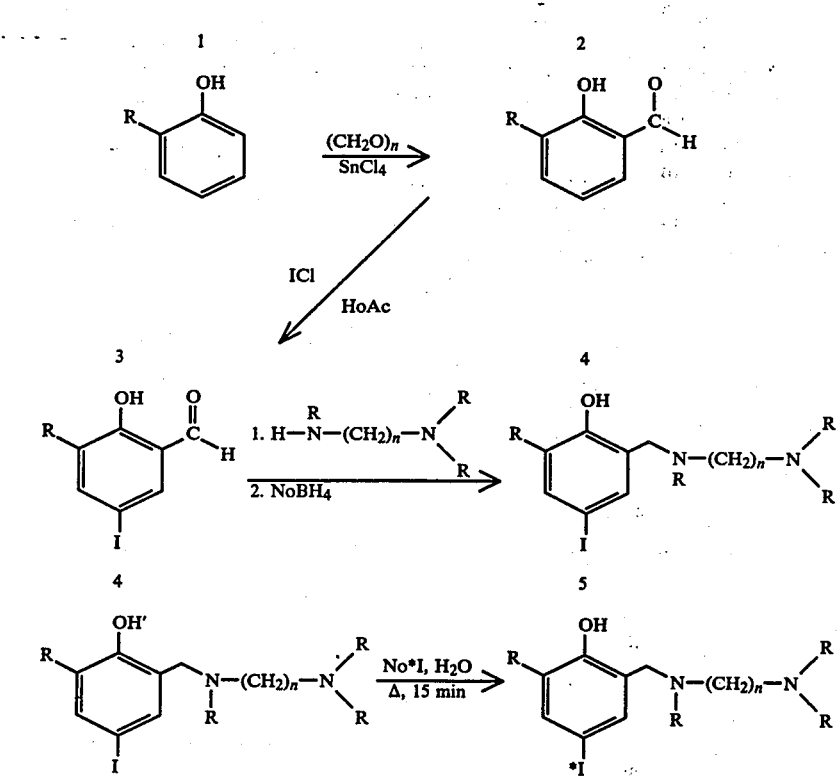

>95% Radiochemical Yield
(Typically 98-99%)

Synthesis of 3-Alkyl-salicylaldehydes (2)

To a stirred solution of the appropriate alkyl phenol (200 mmol) (1) and tributylamine (14.8 g, 80 mmol) in 100 ml of toluene under a nitrogen atmosphere was added anhydrous SnCl$_4$ (5.2 g, 20 mmol) via glass syringe. The mixture was stirred at room temperature for 30 minutes. Paraformaldehyde (13.32 g, 440 mmol) was added and the resulting suspension was heated at 95° for 18 hours. The reaction mixture was allowed to cool and poured into 2 L of water. The mixture was acidified to pH 2 with 4 N HCl and extracted twice with ether. The organics were washed with saturated NaCl, dried over Na$_2$SO$_4$ and evaporated under reduced pressure to give the crude salicylaldehydes as liquids. Kugelrohr distillation (0.5–0.8 mm) at 50°–100° gave the product 2 which was contaminated with 5–15% of the starting phenols (1). These aldehydes were of sufficient purity to carry through the synthesis to the next step.

Synthesis of 5-Iodo-3-alkyl-salicylaldehydes (3)

A solution of ICl (24.3 g, 150 mmol) in 60 ml of glacial acetic acid was added dropwise to a stirred solution of the appropriate salicylaldehyde (2) in 60 ml of glacial acetic acid. After the addition was completed, the dark mixture was heated for 4 hours and then stirred at room temperature overnight. The reaction mixture was poured into 500 ml of water and the product was extracted with two portions of CH$_2$Cl$_2$. The CH$_2$Cl$_2$ extracts were combined, washed with saturated Na$_2$S$_2$O$_3$, dried over Na$_2$SO$_4$ and concentrated under reduced pressure to give a dark brown oil. The oil was filtered through silica gel and eluted with 70% pet ether (bp. 30°–60°)—CHCl$_3$ to give the iodo-salicylaldehydes 3 (75–81%). These compounds decomposed on standing and, hence, were used immediately after chromatography in the next reaction.

Synthesis of N,N-dimethyl-N'-[2-hydroxy-3-alkyl-5-iodobenzyl]-1,3-propanediamines (4)

A solution of the crude aldehyde (3) (3.4 mmol) and 3-dimethylaminopropylamine (2.4 g, 3.9 mmol) in benzene was refluxed, under a Dean-Stark head to effect the separation of water, for 2 hours. The solvent was evaporated under reduced pressure to give a yellow oil. The oil was dissolved in ethanol and NaBH$_4$ (39 mg, 10.3 mmol) was added by spatula in small portions over 20 minutes. The reaction mixture was stirred at room temperature for 18 hours. The resulting clear solution was concentrated under reduced pressure and water (100 ml) was added. The product was extracted with CH$_2$Cl$_2$. The organic layer was washed with saturated NaCl, dried over Na$_2$SO$_4$ and evaporated under reduced pressure to give a clear oil. The oil was converted to the dihydrochloride salt by passing dry HCl gas through a meathanol solution. Evaporation of the methanol gave the crude dihydrochloride salt of the diamine (4) which was recrystallized from acetone-MeOH.

Exchange Radiolabeling of the N,N-dimethyl-N'[2-hydroxy-3-alkyl-5-iodobenzyl]-1,3-propanediamines (5) with I-123

A solution of the diamine (4) (1 mg) and 800–1000 $\mu$Ci of I-123 as NaI in 1 ml of 0.01 N HCl, in a sealed 10 ml serum vial, was heated in a boiling water bath for 15 minutes at ambient pressure. The cooled reaction mixture was analyzed for radiochemical incorporation of TLC in two systems (Merck Silica Gel 60, CHCl$_3$—EtOH—NH$_4$OH, 8:1.5:0.5; Gelman ITLC<CHCl$_3$—EtOH—NH$_4$OH, 8.5:1:0.5). In all cases the radiochemical incorporation was greater than 95%. The mixture was diluted with 1 ml of 0.9% saline and passed through a 0.22 micron filter. The isolated radiochemical yield was greater than 90% based on starting radioiodide.

The group of iodine-123 labeled diamines of the invention typically are any of the labeled compounds as set forth below:

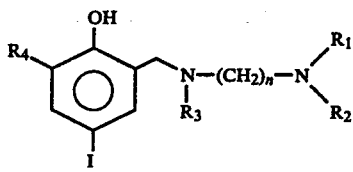

In the compounds of the invention, $R_1$, $R_2$, $R_3$ and $R_4$ may be any alkyl in straight or branched configuration having between 1 and about 10 carbon atoms. A preferred amount of carbon is between 1 and 6 for selective absorption and retention by brain tissue. A preferred number of carbons is between 2 and about 6 carbons for good absorption and retention by brain tissue. $R_1$, $R_2$, $R_3$ and $R_4$ are frequently all CH$_3$. n may be an integer between 1 and about 20. n is commonly 3.

A preferred material is given by the formula below:

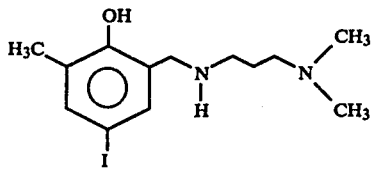

The material is preferred as it allows good brain absorption and retention of the compound. The optimum (most preferred) material is the material as given by the formula below:

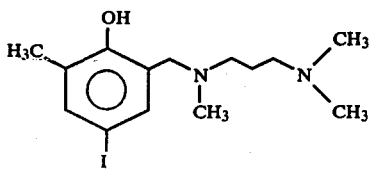

This material is optimum as it is very readily absorbed and retained by the brain and is stable.

While described as particularly preferred for radiopharmacy for photo emission computed tomography of the brain, the compound also finds other uses in radiopharmacy. Typical of other isotope imaging uses of the compound other than in the brain are for solid tumor imaging. It may also be used for other techniques than SPECT in brain imaging such as gamma camera imaging.

As set forth above, it is anticipated that this invention will find particular utility when distributed in kit form to nuclear medicine clinics where the radioactive substitution would take place. The substitution at a clinic would allow iodine-123 to be purchased from any of many sources of the I-123 compound. The radioactive iodine-123 would be purchased when needed, but the kit could be stored in the clinic until such time as substitution was needed to use the compound of the invention in imaging. A typical kit would comprise three components. The first component would be the nonradioactive compound of the invention. The compound of the invention is provided in an acidified solution normally of hydrochloric acid. The second would be a sodium hydroxide fortified buffered solution. Normally sodium phosphate is used as the buffer. A kit finally optionally may consist of a 0.22 micron sterile filter which would be a third component of the kit, if I-123 was obtained from a non-sterile source. The kit also could include utensils for boiling the solution in sterile water and for dilution prior to injection.

In use the radioactive I-123 iodine is mixed with the hydrochloric acid acidified nonradioactive compound of the invention in a vial which forms the first component of the kit. The solution is then heated by being placed in boiling water. Normally, the time in boiling water would be about 15 minutes to exchange the iodine-123 radioiodide into the compound structure. The pH has been adjusted with the buffered sodium hydroxide to a suitable pH for injection into a mammal. The buffered solution is then drawn into a syringe, the disposable filter is attached to the syringe in the I-123 is from a non-sterile source and the solution is passed through the filter into a sterile serum vial from which it may be removed for injection into the warm blooded mammal being treated.

The radiopharmaceutical compounds of the invention possess lipid solubility characteristics significantly dependent on pH in at least the 6.6 to 7.6 pH range and particularly in the 7.0 to 7.4 pH range. The regional pH shift in all the presently known target organs or tissues is toward a lower pH than the normal pH of the blood. The compounds of the present invention show increasing lipid solubility and therefore increasing cell wall penetrating capability with increasing pH in the 6.6 to about 7.6 pH range. The compounds of the invention are believed to penetrate the cell walls by passive diffusion. The accumulation of the radiopharmaceutical compounds principally depended on the intracellular pH of the target tissue, rather than the similarity to a metabolite for which an active or facilitated transport mechanism exists. After having penetrated the target organ such as the brain having a regional pH shift, the compound is effectively trapped in the cells of the target because it is less lipid soluble at the pH of the target than at the pH of the blood. Blood pH is about 7.4. Consequently, a rate of egress of the compound bipassed at diffusion from the target is significantly lower than its rate of entry, i.e. the rapid return of the compound to the blood is prevented, which results in accumulation of the compound in the target.

It has been found that conventional n-octanol-aqueous medium partition coefficients at several pH values of the aqueous medium provide excellent indicia to determine the sufficient lipophilicity of a radiopharmaceutical compound at pH 7.4 to permit passage of the compound from the blood into the target organ or tissue and the insufficient lipophilicity to prevent rapid return of the compound from the target organ or tissue to the blood at pH 7.0. The n-octanol-aqueous medium partition coefficients of the compound are readily measured in accordance with standard practice in the prior art. Briefly, such measurements include the steps of dissolving a known amount of the compound in an aqueous buffer of a predetermined pH and extracting the buffer solution with a known amount of n-octanol until an equilibrium of distribution of the compound between the aqueous and n-octanol phases occurs. The concentration of the compound in both phases is then measured by suitable analytical means, such as ultraviolet spectrophotometry; the partition coefficient being the ratio of the two measured concentrations.

For the purposes of evaluating a plurality of radioactive compounds for use in the novel method of the present invention, the n-octanol-aqueous medium partition coefficients of the compounds were measured in the following manner. The radioactive compound was mixed with 1.0 ml of n-octanol and 1.0 ml of buffer of the desired predetermined pH. The radioactivity of this mixture was counted, and the mixture was placed in a water bath shaker at 37° C. for 2 hours. After centrifugation at 3,000 rpm for 5 minutes, the n-octanol layer was separated and its radioactivity counted. The partition coefficient of the compound was calculated by the following equation:

$$\text{Partition Coefficient} = \frac{\text{counts in n-octanol}}{\text{initial counts} - \text{counts in n-octanol}}$$

Partition coefficients obtained in this manner for the optimum radiopharmaceutical compound of the present invention are shown on the graph of FIG. 1. The results indicate excellent change in lipophilicity at the pH required for entry and retention in body organs.

Studies of distribution of the optimum radiopharmaceutical compound of the present invention in rats, the results of which are reflected in Table 1, were conducted according to standard practice in the pharmacological sciences, and therefore need not be described here in great detail. Nevertheless, for the sake of complete understanding of the present invention, some experimental details of these studies are briefly described below:

Sprague-Dawley male rats (220–300 g) were injected intravenously (femoral vein) with a 0.2 ml solution (0.5–20. micro Ci) under light ether anaesthesia. At different time periods after the injection, the animals were sacrificed and organs of interest were excised and counted in a well counter. Percent dose was estimated by comparison of tissue counts to suitably diluted aliquots of the injected material. Total activities in blood and muscle were calculated by assuming that they are 7% and 40% of the body weight respectively.

EXAMPLE

Synthesis of 3-Methyl-salicylaldehydes

To a stirred solution of the o-cresol (200 mmol) and tributylamine (14.8 g, 80 mmol) in 100 ml of toluene under a nitrogen atmosphere was added anhydrous $SnCl_4$ (5.2 g, 20 mmol) via glass syringe. The mixture was stirred at room temperature for 30 minutes. Paraformaldehyde (13.32 g, 440 mmol) was added and the resulting suspension was heated at 95° for 18 hours. The reaction mixture was allowed to cool and poured into 2 L of water. The mixture was acidified to pH 2 with 4 N HCl and extracted twice with ether. The organics were washed with saturated NaCl, dried over $Na_2SO_4$ and evaporated under reduced pressure to give the crude salicylaldehydes as liquids. Kugelrohr distillation (0.5–0.8 mm) at 50°–100° gave the product which was contaminated with 5–15% of the o-cresol. These aldehydes were of sufficient purity to carry through the synthesis to the next step.

Synthesis of 5-Iodo-3-methyl-salicylaldehydes (3)

A solution of ICl (24.3 g, 150 mmol) in 60 ml of glacial acetic acid was added dropwise to a stirred solution of 3-methyl salicylaldehyde in 60 ml of glacial acetic acid. After the addition was completed, the dark mixture was heated for 4 hours and then stirred at room temperature overnight. The reaction mixture was poured into 500 ml of water and the product was extracted with two portions of $CH_2Cl_2$. The $CH_2Cl_2$ extracts were combined, washed with saturated $Na_2S_2O_3$, dried over $Na_2SO_4$ and concentrated under reduced pressure to give a dark brown oil. The oil was filtered through silica gel and eluted with 70% pet ether (bp. 30°–60°)—$CHCl_3$ to give the iodo-salicylaldehydes (75–81%).

Synthesis of N,N-dimethyl-N'-[2-hydroxy-3-methyl-5-iodobenzyl]-1,3-propanediamines (4)

A solution of 5-iodo-3-methyl-salicylaldehyde (3.4 mmol) and N,N-Dimethyl-N'-methyl-1,3-propanediamine (2.4 g, 3.9 mmol) in benzene was refluxed, under a Dean-Stark head to effect the separation of water, for 2 hours. The solvent was evaporated under reduced pressure to give a yellow oil. The oil was dissolved in ethanol and $NaBH_4$ (39 mg, 10.3 mmol) was added by spatula in small portions over 20 minutes. The reaction mixture was stirred at room temperature for 18 hours. The resulting clear solution was concentrated under reduced pressure and water (100 ml) was added. The product was extracted with $CH_2Cl_2$. The organic layer was washed with saturated NaCl, dried over $Na_2SO_4$ and evaporated under reduced pressure to give a clear oil. The oil was converted to the dihydrochloride salt by passing dry HCl gas through a methanol solution. Evaporation of the methanol gave the crude dihydrochloride salt of the diamine which was recrystallized from acetone-MeOH.

Exchange Radiolabeling of the N,N,N-trimethyl-N'[2-hydroxy-3-methyl-5-iodobenzyl]-1,3-propanediamines (5) with I-123.

A solution of the diamine (1 mg) and 1–10 uCi of I-123 as NaI, no carrier added in 1 ml of 0.01 N HCl, in a sealed 10 ml serum vial, was heated in a boiling water bath for 15 minutes at ambient pressure. The cooled reaction mixture was analyzed for radiochemical incorporation by TLC in two systems (Merck Silica Gel 60, $CHCl_3$—EtOH—$NH_4OH$, 8:1.5:0.5; Gelman ITL-C<$CHCl_3$—EtOH—$NH_4OH$, 8.5:1:0.5). In all cases the radiochemical incorporation was greater than 95%. The mixture was diluted with 1 ml of 0.9% saline and passed through a 0.22 micron filter. The isolated radiochemical yield was greater than 90% based on starting radioiodide.

Sprague-Dawley male rats (220–300 g) under light ether anesthesia were injected intravenously with 0.2 ml of a saline solution containing 0.5–20 uCi of test compound (specific activity 0.5–1.0 uCi/mg). At different time periods after injection the animals were put under ether anesthesia and killed by cardiactomy. The organs of interest were excised, weighed and counted in a Beckman automatic gamma counter (Model 4000).

The % dose/organ was determined by comparison of tissue radioactivity levels to suitably diluted aliquots of the injected dose. The approximate % dose/g of wet tissue or organ can be calculated by dividing the % dose/organ by the mean organ weight (mean weights: heart 0.85 g, brain 1.65 g, blood 18 g, liver 9 g, kidneys 1.9 g, lungs 1.6 g). The brain to blood concentration ratios was calculated from the %dose/gram of wet tissue and are set forth in Table 1 below.

TABLE 1

| Biodistribution of I-123 Compound in rats (% dose/organ, average of 3 rats) | | |
|---|---|---|
| | 2 min | 1 hr |
| Blood | 2.02 | 0.85 |
| Muscle | 5.66 | 12.77 |
| Heart | 2.71 | 0.29 |
| Lungs | 36.53 | 18.25 |
| Kidneys | 8.06 | 2.87 |
| Spleen | 0.72 | 1.58 |
| Liver | 5.52 | 4.68 |
| Stomach | 0.80 | 0.93 |
| Skin | 6.73 | 9.21 |
| Thyroids | 0.59 | 0.06 |
| Brain | 2.74 | 2.50 |
| Blood/Brain | 14.84 | 32.18 |

As can be seen from Table 1, there is a high initial uptake of the material in the brain, lung and liver. The uptake persists sufficiently to allow imaging.

The invention has been described with reference to specific materials and formation methods. However, it is within the invention to form the compounds by any suitable method. Further, while the invention has been described primarily for use in imaging of the brain, it is also suitable for imaging other organs, such as the lungs and solid tumors. Further, while the kit for utilization in forming the radioactive compounds of the invention was described with two components it is within the invention to provide other diluent or treatment materials for combination with the device of the invention. For instance, a treatment material could be combined with the compound of the invention prior to injection. Further, the compound of the invention could be combined with other radiopharmaceuticals for different or enhanced imaging effects.

We claim:

1. An Iodinated phenolic amine having the general formula:

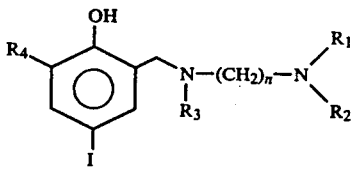

wherein $R_1$, $R_2$, $R_3$ and $R_4$ are independently a straight or branched alkyl radical having between 1 and 10 carbons and n is an integer having a value between 1 and 20.

2. The compound of claim 1 wherein n is an integer between 2 and 6 and $R_1$, $R_2$, $R_3$ and $R_4$ are between 1 and 6.

3. The compound of claim 1 wherein $R_1$, $R_2$, $R_3$ and $R_4$ are each $CH_3$.

4. The compound of the claim 3 wherein n is the integer 3.

5. The compound of claim 1 wherein the I comprises radioactive iodine-123.

6. The compound of claim 1 wherein said I is not radioactive.

7. The compound of claim 1 wherein n is the integer 3; $R_1$, $R_2$ and $R_4$ are each $CH_3$ and $R_3$ is H.

8. A method for selectively depositing a radiopharmaceutical compound having radiation readily observable by radiation detecting means into at least one target tissue or organ of a mammal, the target tissue organ having a physiologically significantly different intercellular pH that the blood of the mammal, the method comprising the step of introducing into the blood stream of a mammal, a radiopharmaceutical compound having the general formula:

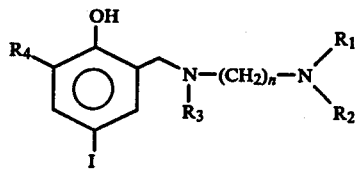

wherein $R_1$, $R_2$, $R_3$ and $R_4$ are independently between 1 and 10 carbons and n is an integer between 1 and 20.

9. The method of claim 8 wherein n is an integer between 2 and 6 and $R_1$, $R_2$, $R_3$ and $R_4$ are between 1 and 6 carbon atoms.

10. The method of claim 8 wherein $R_1$, $R_2$, $R_3$ and $R_4$ are each $CH_3$.

11. The method of claim 10 wherein n is the integer 3.

12. The method of claim 8 wherein the I comprises radioactive iodine-123.

13. The method of claim 8 wherein n is the integer 3, $R_3$ is H and $R_1$, $R_2$ and $R_4$ are each $CH_3$.

14. A method for selectively depositing a radiopharmaceutical compound emitting radiation readily observable by radiation detecting means in at least one target tissue or organ of a mammal, said target tissue organ having a physiologically significantly different intercellular pH than the blood of the mammal, the method comprising the steps of providing radioactive iodine-123, providing an iodinated phenolic amine of the general formula:

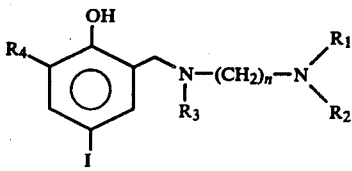

wherein $R_1$, $R_2$, $R_3$ and $R_4$ are independently between 1 and 10 carbons and n is an integer between 1 and 20, mixing radioactive iodine-123 and the non-radioactive iodinated phenolic amine, heating the mixture for a sufficient time and to sufficient temperature for said radioactive iodine to substitute in said iodinated phenolic amine and introducing the substituted compound into the mammal.

15. The method of claim 14 wherein n is an integer between 2 and 6 and $R_1$, $R_2$, $R_3$ and $R_4$ are between 1 and 6 carbon atoms.

16. The method of claim 14 wherein $R_1$, $R_2$, $R_3$ and $R_4$ are each $CH_3$.

17. The method of claim 16 wherein n is the integer 3.

18. The method of claim 14 wherein said heating is for about 15 minutes at about 100° C.

19. The method of claim 14 wherein the substituted material is filtered prior to being introduced into said mammal.

20. The method of claim 14 wherein all materials for the method are available in a kit except the iodine-123.

21. The method of claim 14 wherein n is the integer 3, $R_3$ is H and $R_1$, $R_2$ and $R_4$ are each $CH_3$.

22. An article for preparation of a radiopharmaceutical iodinated phenolic amine comprising a container of an iodinated phenolic amine having the general formula:

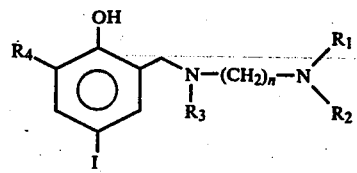

wherein $R_1$, $R_2$, $R_3$ and $R_4$ are independently at each occurrence a straight or branched alkyl radical having between 1 and 20 carbons and n is an integer having a value between 1 and 10 and a container of a sodium phosphate buffer.

23. The article of claim 22 wherein n is an integer between 2 and 6 and $R_1$, $R_2$, $R_3$ and $R_4$ are between 1 and 6 carbon atoms.

24. The article of claim 22 wherein $R_1$, $R_2$, $R_3$ and $R_4$ each comprise $CH_3$.

25. The article of claim 24 wherein n is the integer 3.

26. The article comprising claim 24 further comprising a sterile filter.

27. The article of claim 22 wherein $R_1$, $R_2$ and $R_4$ are each $CH_3$ and $R_3$ is H.

* * * * *